United States Patent
Ikeda (10) Patent No.: US 9,949,670 B2
(45) Date of Patent: Apr. 24, 2018

(54) EAR MODEL, HEAD MODEL, AND MEASURING APPARATUS AND MEASURING METHOD EMPLOYING SAME

(71) Applicant: KYOCERA CORPORATION, Kyoto (JP)

(72) Inventor: Tomoyoshi Ikeda, Kanagawa (JP)

(73) Assignee: KYOCERA Corportion, Kyoto (JP)

( * ) Notice: Subject to any disclaimer, the term of this patent is extended or adjusted under 35 U.S.C. 154(b) by 573 days.

(21) Appl. No.: 14/355,546

(22) PCT Filed: Jul. 25, 2013

(86) PCT No.: PCT/JP2013/004539
§ 371 (c)(1),
(2) Date: Apr. 30, 2014

(87) PCT Pub. No.: WO2014/020873
PCT Pub. Date: Feb. 6, 2014

(65) Prior Publication Data
US 2015/0128708 A1    May 14, 2015

(30) Foreign Application Priority Data
Jul. 31, 2012 (JP) .................. 2012-170492

(51) Int. Cl.
*A61B 5/12* (2006.01)
*H04M 1/24* (2006.01)
(Continued)

(52) U.S. Cl.
CPC ................. *A61B 5/12* (2013.01); *H04M 1/24* (2013.01); *H04M 1/04* (2013.01); *H04R 25/30* (2013.01);
(Continued)

(58) Field of Classification Search
CPC . A61B 5/12; H04R 1/00; H04R 29/00; H04R 25/00; H04S 1/00; H04M 1/04; H04M 1/24
(Continued)

(56) References Cited

U.S. PATENT DOCUMENTS 5,624,377 A    4/1997  Davis
7,197,911 B1 *  4/2007  Lilienfeld .............. G01N 21/51
                                                        73/24.03
(Continued)

FOREIGN PATENT DOCUMENTS

CN    101785327 A     7/2010
EP    2182510 A1 *    5/2010   ........... G10K 11/178
(Continued)

OTHER PUBLICATIONS

International Search Report; PCT/JP2013/004539; dated Oct. 15, 2013.
(Continued)

*Primary Examiner* — Hezron E Williams
*Assistant Examiner* — Tarun Sinha
(74) *Attorney, Agent, or Firm* — Studebaker & Brackett PC (57) ABSTRACT

Provided is a measuring apparatus that may measure a vibration amount weighted by cartilage conduction characteristics of the human ear and thus allows for accurate evaluation of an electronic device having a vibrator. A measuring apparatus for evaluating an electronic device that delivers a sound through vibration transmission from a vibrator retained in a housing held against the human ear includes an ear simulator simulating the human ear and a vibration detector disposed on an artificial eardrum formed in the ear simulator.

28 Claims, 6 Drawing Sheets (51) Int. Cl.
*H04R 25/00* (2006.01)
*H04R 29/00* (2006.01)
*H04M 1/04* (2006.01)

(52) U.S. Cl.
CPC ........ *H04R 29/001* (2013.01); *H04R 2499/11* (2013.01)

(58) Field of Classification Search
USPC .......................................................... 73/585
See application file for complete search history.

(56) References Cited

U.S. PATENT DOCUMENTS

| | | | |
|---|---|---|---|
| 8,340,310 B2 | 12/2012 | Ambrose et al. | |
| 8,737,635 B2 | 5/2014 | Ambrose et al. | |
| 2004/0073136 A1* | 4/2004 | Thornton | A61B 5/12 600/559 |
| 2006/0126855 A1* | 6/2006 | Geiger | H04R 5/027 381/56 |
| 2008/0050710 A1 | 2/2008 | Cottler et al. | |
| 2009/0028356 A1* | 1/2009 | Ambrose | H04R 1/1091 381/71.6 |
| 2010/0177910 A1* | 7/2010 | Watanabe | H04R 5/033 381/94.1 |
| 2011/0164757 A1* | 7/2011 | Sibbald | H04R 29/001 381/58 |
| 2011/0183664 A1* | 7/2011 | Topaltzas | H04M 1/24 455/425 |
| 2013/0188801 A1 | 7/2013 | Ambrose et al. | |

FOREIGN PATENT DOCUMENTS

| | | |
|---|---|---|
| GB | 2456846 A | 7/2009 |
| JP | 58-198338 A | 11/1983 |
| JP | 03-168000 A | 7/1992 |
| JP | 06-038359 U | 5/1994 |
| JP | 11-500284 A | 1/1999 |
| JP | 2005-348193 A | 12/2005 |
| JP | 4237424 B2 | 3/2009 |
| WO | 2004/092700 A2 | 10/2004 |

OTHER PUBLICATIONS

The extended European search report issued by the European Patent Office dated Mar. 15, 2016, which corresponds to European Patent Application No. 13825567.4-1972 and is related to U.S. Appl. No. 14/355,546.

Søren Jønsson et al.; "Application Note Improving Telephone Handset Performance—On the Use of Ear Simulators ITU-T p. 57 Type 1 and Type 3.2 for Telephonometric Measurements"; Brüel & Kjær; Jun. 2011, pp. 1-12; Denmark.

Nokia; "Proposal for additional HATS handset position definition for the Type 3.3 artificial ear in ITU-T Recommendation p. 64"; Internationl Telecommunication Union; Jan. 2007; pp. 1-17; vol. 5/12; Geneva, CH.

S.Reinfeldt et al.; "Examination of bene-conducted transmission from sound field excitation measured by thresholds, ear-canal sound pressure, and skull vibrations"; The Journal of the Acoustical Society of America; May 2007; pp. 1576-1587; vol. 121; No. 3; New York, US.

Voicequalitylabs; "DHP-501 Dynamic Handset Positioner"; Jun. 6, 2012. Retrieved from the Internet; URL:https://www.youtube.com/watch?v=3J77q23KCdw.

Office Action issued by the Chinese Patent Office dated Jan. 4, 2017, which corresponds to Chinese Patent Application No. 2016122901804290; 24pp.

An Office Action, "Notification of the Second Office Action" issued by Chinese Patent Office dated Aug. 30, 2017, which corresponds to Chinese Patent Application No. 201380028936.9; with English translation.

* cited by examiner

EAR MODEL, HEAD MODEL, AND MEASURING APPARATUS AND MEASURING METHOD EMPLOYING SAME

CROSS REFERENCE TO RELATED APPLICATION

This application claims priority to and the benefit of Japanese Patent Application No. 2012-170492 filed on Jul. 31, 2012, the entire contents of which are incorporated herein by reference.

TECHNICAL FIELD

The present invention relates to a measuring apparatus and a measuring method used for evaluation of an electronic device that delivers a sound through vibration transmission from a vibrator retained in a housing held against the human ear, and also to an ear model and an artificial head model employed for the measuring apparatus.

BACKGROUND

Patent Document 1 describes an electronic device such as a mobile phone that delivers an air conduction sound and a bone conduction sound to a user. Patent Document 1 also describes that the air conduction sound is a sound transmitted to the auditory nerve of the user when vibrated air caused by vibration of an object is transmitted to the ear drum via the ear canal and the ear drum vibrates. Patent Document 1 further describes that the bone conduction sound is a sound transmitted to the auditory nerve of the user via a part of the body of the user (the cartilage of the ear, for example) who is touching an vibrating object.

Patent Document 1 describes that a vibrator in the shape of a short rectangular plate formed of a piezoelectric bimorph and a flexible material is attached to an outer surface of the housing of the phone via an elastic member. Patent Document 1 also describes that, upon application of a voltage on the piezoelectric bimorph of the vibrator, a piezoelectric material stretches in a longitudinal direction causing bending vibration of the vibrator and, when the user makes the vibrator contact the auricle, the air conduction sound and the bone conduction sound are transmitted to the user.

CITATION LIST

Patent Document 1: Japanese Patent Application Laid-Open Publication No. 2005-348193

SUMMARY

Incidentally, as described in Patent Document 1, in order to evaluate the electronic device that delivers the air conduction sound and, via the cartilage of the external ear, the bone conduction sound, it is necessary to measure a sound pressure and a vibration amount of vibration generated by vibration of the vibrator that approximately act on the auditory nerve of the human body.

The present invention aims to provide the ear model and the head model that may measure the vibration amount weighted by the vibration transmission characteristics of the human ear and thus allow for accurate evaluation of the electronic device having the vibrator, and also to provide the measuring apparatus and the measuring method employing those models.

The present invention relates to a measuring apparatus including:
an ear simulating unit for simulating the human ear and having an artificial eardrum and a vibration detector disposed on the artificial eardrum formed in the ear simulating unit, such that the electronic device delivers a sound through vibration transmission from a vibrator retained in a housing held against the human ear.

According to the present invention, the vibration amount in consideration of vibration transmission characteristics of the human ear may be measured, whereby the electronic device having the vibrator may be accurately evaluated.

DESCRIPTION OF EMBODIMENTS

To measure a sound pressure and a vibration amount of vibration generated by vibration of the vibrator that approximately act on the auditory nerve of the human body, the following two methods are known as measuring methods of the vibration amount.

A first measuring method measures the vibration amount, as the voltage, obtained by holding a vibrator to be measured against an artificial mastoid for measurement of a bone conduction vibrator mechanically simulating the mastoid part behind the ear. A second measuring method measures the vibration amount, as the voltage, obtained by holding a vibration pickup such as a piezoelectric accelerometer pickup and the like against the vibrator to be measured.

However, the voltage measured by the first measuring method described above is not weighted by vibration transmission characteristics displayed when the vibrator is held against the human ear but mechanically weighted by human body characteristics that is displayed when the vibrator is held against the mastoid part behind the human ear. Also, the voltage measured by the second measuring method is obtained by direct measurement of the vibration amount of the vibrator and, as with the first measuring method, the measured voltage is not weighted by the vibration transmission characteristics of the human ear described above. Therefore, measurements of the vibration amount of the vibrator by employing the known measuring methods lead to an inaccurate evaluation of the electronic device.

Hereinafter, in light of the above viewpoint, embodiments of the present invention will be described with reference to the accompanying drawings.

First Embodiment

Figure 1:
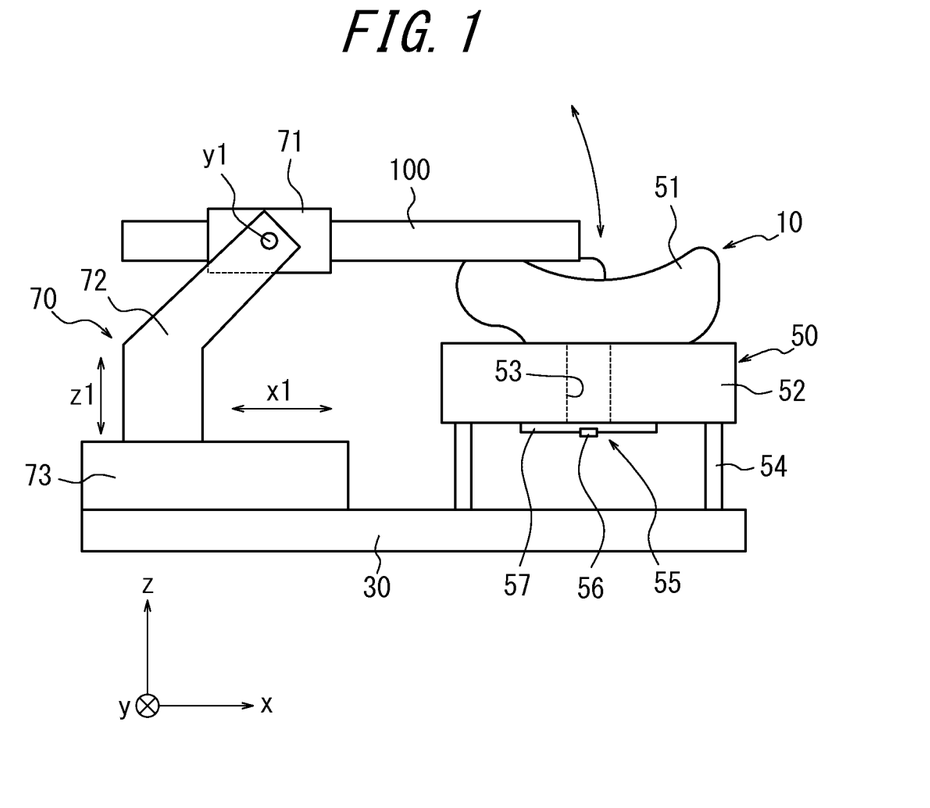
FIG. 1 is a diagram illustrating a schematic configuration of a measuring apparatus according to a first embodiment of the present invention.
Figure 2:
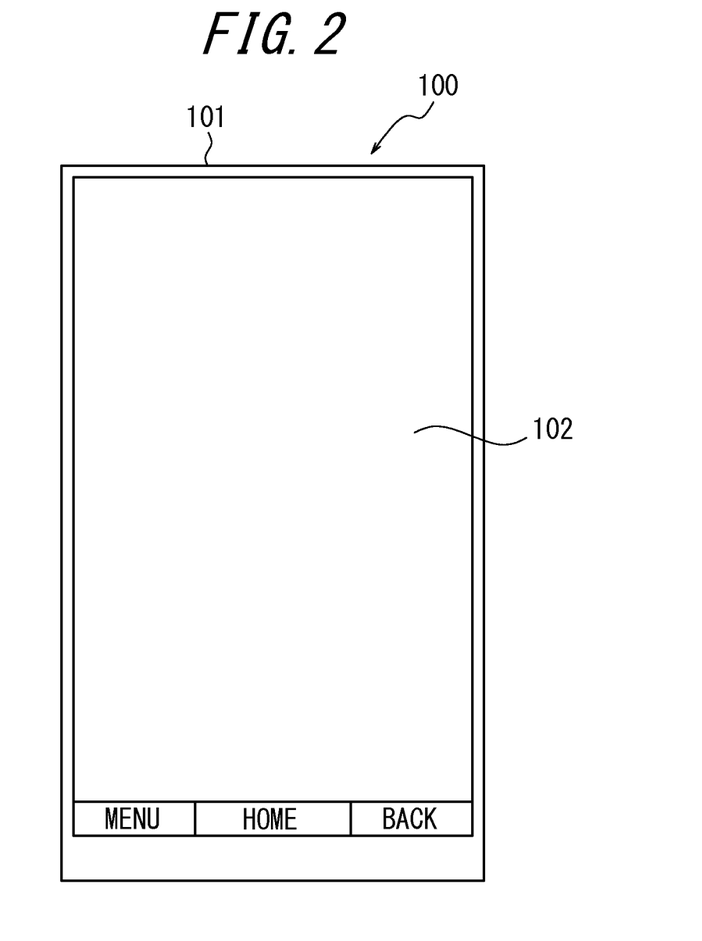
FIG. 2 is a plan view illustrating an example of an electronic device to be measured.

FIG. 1 is a diagram illustrating a schematic configuration of a measuring apparatus according to a first embodiment of the present invention. A measuring apparatus 10 of the present embodiment includes an ear simulator 50 supported on a base 30 and a holder 70 for holding an electronic device 100 to be measured. In the following description, as illustrated in a plan view of FIG. 2, the electronic device 100 is a mobile phone such as a smart phone having, on a rectangular surface thereof, a rectangular panel 102 that is larger than the human ear and functions as a vibrator. First, the ear simulator 50 will be described.

The ear simulator 50 is a model of the human ear and includes an ear model 51, an artificial ear canal unit 52 coupled to, or integrally formed with, the ear model 51, and an artificial eardrum 57 coupled to, or integrally formed with, the artificial ear canal unit 52. The artificial ear canal unit 52 is in size covering the ear model 51 and has an artificial ear canal 53 formed in a central portion thereof. The ear simulator 50, at a periphery of the artificial ear canal unit 52, is supported on the base 30 via a support member 54.

The ear simulator 50 may be formed of a material similar to that of common ear models used for, for example, a human body model of HATS (Head And Torso Simulator) and KEMAR (an electronic mannequin for acoustic researches produced by Knowles Electronics), that is, a material in conformity with, for example, IEC 60318-7. This material may be formed of, for example, rubber with Shore hardness of 35 to 55. That is, the ear model of the human body model described above is divertible to an auricular portion.

A thickness of the artificial ear canal unit 52, that is, a length of the artificial ear canal 53 corresponds to a length to the human eardrum (cochlea) and is appropriately set in a range of, for example, 20 mm to 40 mm. According to the present embodiment, the length of the artificial ear canal 53 is set to approximately 30 mm.

The artificial eardrum 57 is formed closing the artificial ear canal 53 at an end of the artificial ear canal unit 52 in such a manner that vibration from the artificial ear canal 53 is transmitted to the artificial eardrum 57.

The artificial eardrum 57 is formed of a material similar to that of the common ear models used for, for example, the human body model of HATS and KEMAR, that is, the material in conformity with, for example, IEC 60318-7 and has a thin film shape. A thickness of the artificial eardrum 57 may be approximately, for example, 0.05 mm to 2 mm to allow for reproduction of a response to vibration of the human eardrum. Also, an area of a portion of the artificial eardrum 57 in contact with a space inside the artificial ear canal 53 is in size similar to an average size of the human eardrum and has a circular, elliptical, or rectangular shape of approximately, for example, 0.5 $cm^2$ to 2.5 $cm^2$.

The artificial eardrum 57 is not limited to be formed of the material and to have the thickness described above but may be formed of a biomaterial having, as a main component, a polymer aminoglycoside extracted from a shell of a red snow crab, which is a material commonly used for the artificial eardrum, or a biomaterial having, as a main component, a component obtained by purifying collagen of calf dermis. Also, instead of attaching the artificial eardrum formed of those biomaterials to the artificial ear canal unit 52, the artificial eardrum may be formed by using the materials in conformity with IEC 60318-7 described above and the thickness and the size thereof may be adjusted so as to approximate physical properties of the artificial eardrum formed of the biomaterials described above. Alternatively, materials conventionally used as eardrum perforation restorative materials such as natural origin products or processed products such as rubber film, a rubber ball, a piece of paper, collodion membrane, egg film, cellophane, polytetrafluoroethylene, silicone membrane, collagen, fibrin film, and the like. The artificial eardrum 57 formed of those materials may be fixed blocking the artificial ear canal 53 at the end of the artificial ear canal unit 52 by using an adhesive selected considering the materials of the artificial ear canal unit 52 and the artificial eardrum 57. Needless to say, the artificial eardrum 57 may be integrally molded with other parts of the ear model such as the artificial ear canal unit 52 and the ear model 51 by using the same material or a different material.

Figure 3A:
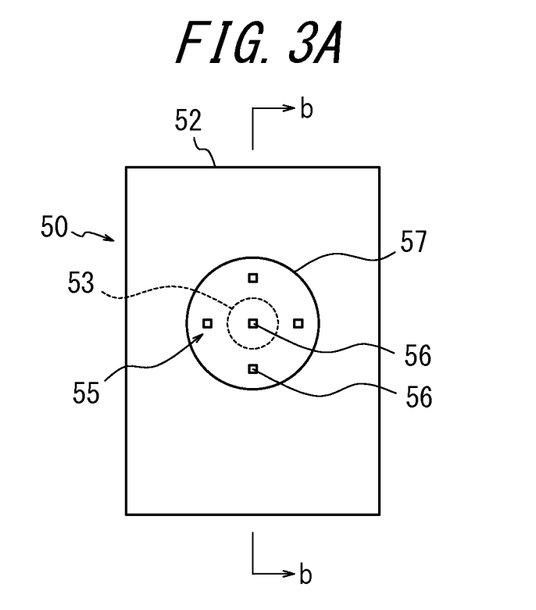
FIGS. 3A and 3B are detailed diagrams of portions of the measuring apparatus in FIG. 1.
Figure 3B:
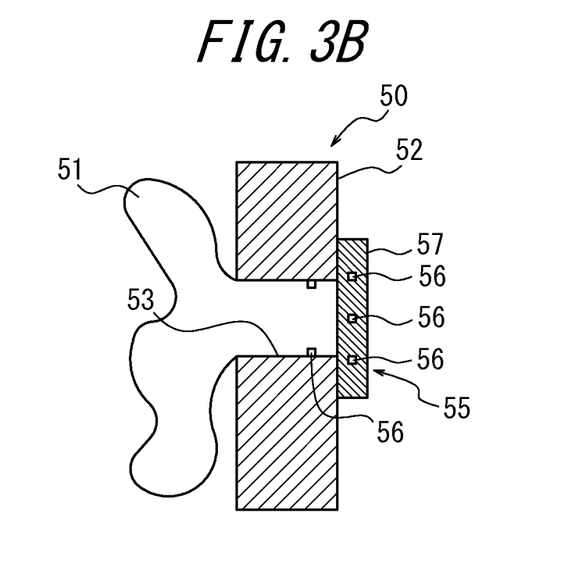

In the ear simulator 50, on an end plane of the artificial ear canal unit 52 opposite to a plane having the ear model 51, a vibration detector 55 is disposed on the artificial eardrum 57. Note that the vibration detector 55 may be disposed on the plane having the ear model 51. The vibration detector 55 has a vibration detection element 56 including, for example, a vibration pickup such as a piezoelectric accelerometer pickup and the like. FIG. 3A is a plan view of the ear simulator 50 viewed from the base 10, and FIG. 3B is a cross-sectional diagram taken from b-b line of FIG. 3A. Although FIG. 3A illustrates a plurality of vibration detection elements 56 in the form of a chip disposed outside the artificial eardrum 57, a plurality of vibration detection elements 56 may be disposed on an inner surface of the artificial ear canal 53 as illustrated in FIG. 3B. When a plurality of vibration detection elements 56 are disposed, they may be arranged at appropriate intervals at a periphery of the artificial eardrum 57 and the artificial ear canal 53. Or, the detection elements 56 having an arc shape may be disposed surrounding a periphery of an opening of the artificial ear canal 53. Note that, although FIG. 3A illustrates the artificial ear canal unit 52 having a rectangular shape, the artificial ear canal unit 52 may have any shape.

The vibration pickup may be, for example, embedded in the artificial eardrum 57 having a lead drawn outside thereof, or attached to the artificial eardrum 57 with an adhesive or the like. Also, as the vibration pickup in the form of a chip, commercially available ones such as, for example, NP-2106 which is ultra-compact lightweight and produced by Ono Sokki Co., Ltd. and PV-08A and PV-90B produced by Rion Co., Ltd. may be appropriately selected. Note that, considering that PV-08A produced by Rion Co., Ltd., for example, weighs approximately 0.7 g and, due to addition of the weight, vibration characteristics of the artificial eardrum 57 becomes different from that of the actual human eardrum, the artificial eardrum 57 may be preliminarily made lightweight. A vibration pickup such as TYPE 7302 produced by ACO Co., Ltd. is lightweight weighing approximately 0.2 g and thus preferable.

Next, the holder 70 will be described. In a case where the electronic device 10 is the mobile phone such as the smart phone having the rectangular shape in a plan view, when a user holds the mobile phone against the ear of the user with one hand, either lateral side of the mobile phone is usually held by the hand. Also, a pressure of the mobile phone applied on the ear and a contact position vary between people (users) and changes while the mobile phone is in use. According to the present embodiment, the electronic device 100 is held simulating such a using manner of the mobile phone.

As such, the holder 70 includes a supporter 71 for supporting either lateral side of the electronic device 100. The supporter 71 is attached to one end of an arm 72 to be rotatable about a y1-axis parallel to a y-axis in a direction holding the electronic device 100 against the ear simulator 50. The other end of the arm 72 is coupled to a movement adjuster 73 provided on the base 30. The movement adjuster 73 may adjust a movement of the arm 72 between an direction x-1 vertical to the electronic device 100 supported by the supporter 71, which is a direction parallel to an x-axis orthogonal to the y-axis, and a direction z-1 to hold the electronic device 100 against the ear simulator 50, which is a direction parallel to a z-axis orthogonal to the y-axis and the x-axis.

Accordingly, by adjusting a rotation of the supporter 71 about the y1-axis, or by adjusting a movement of the arm 72 in a direction z-1, the pressure on the ear simulator 50 applied by the vibrator (panel 102) of the electronic device 100 supported by the supporter 71 is adjusted. According to the present embodiment, the pressure is adjusted in a range of 0 N to 10 N, preferably in a range of 3 N to 8 N. Also, by adjusting the movement of the arm 72 in the direction x-1, the contact position of the electronic device 100 to the ear simulator 50 is adjusted such that, for example, the vibrator (panel 102) covers approximately overall the ear simulator 50 or a partially covers it.

Note that the arm 72 may be configured such that the movement thereof may be adjusted in the direction parallel to the y-axis, or such that a rotation thereof may be adjusted about an axis parallel to the x-axis or the z-axis, whereby the contact position of the electronic device 100 to the ear simulator 50 may be adjusted in a variety of manners. Also, in order to allow for measurements when the vibrator is not a panel but a component positioned on a corner of the housing of the electronic device, the arm 72 may be configured to hold the electronic device such that the corner is held against the ear simulator 50. That is, the arm 72 may freely change an angle and a position of the holder as well as fixing the holder. Such a retention mechanism may be produced, without problems, by combining known mechanisms. Note that each contact position may be detected by using an accelerometer, and a pressure sensor for measuring the pressure on the ear simulator 50 of the measuring apparatus applied by the electronic device may be separately provided around, for example, the auricle of the ear model. Thereby, a correlation between the contact position and the vibration amount, or between the pressure and the vibration amount, may be obtained.

Figure 4:
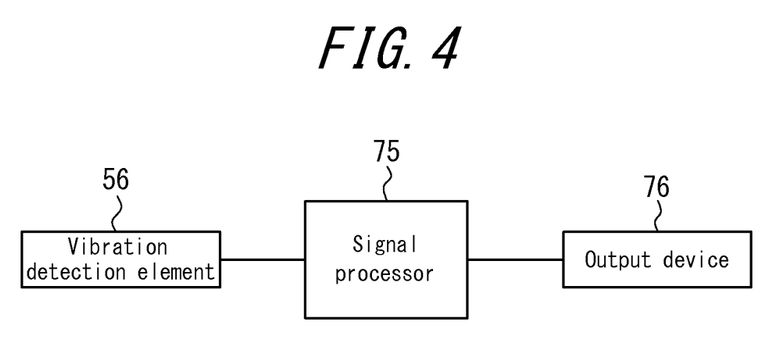
FIG. 4 is a functional block diagram of a main section of the measuring apparatus in FIG. 1.

FIG. 4 is a functional block diagram of a main section of the measuring apparatus 10 according to the present embodiment. The vibration detection element 56 is connected to a signal processor 75 which, based on an output of the vibration detection element 56, measures the vibration amount of the artificial ear canal unit 52 or the artificial eardrum 57 caused by the electronic device 100. The signal processor 75 also measures audibility based on the measured vibration amount. Results of these measurements are output to an output device 76 such as a display unit, a printer, a storage unit and the like, to be used for the evaluation of the electronic device 100.

According to the measuring apparatus 10 of the present embodiment, as described above, a vibration level weighted by vibration transmission characteristics of the human ear may be measured, thus allowing for accurate evaluation of the electronic device 100. Also, by placing a microphone, for example, on the artificial eardrum 57 or inside the artificial ear canal 53, a sound pressure via the artificial ear canal 53 may be measured together with the vibration level. Accordingly, since an auditory level combining the vibration level corresponding to cartilage conduction and a sound pressure level corresponding to the air conduction sound may be measured, the electronic device 100 may be evaluated in further detail. Further, since the contact position as well as the pressure on the ear simulator 50 applied by the electronic device 100 may be varied, the electronic device 100 may be evaluated in a variety of manners.

Second Embodiment

Figure 5:
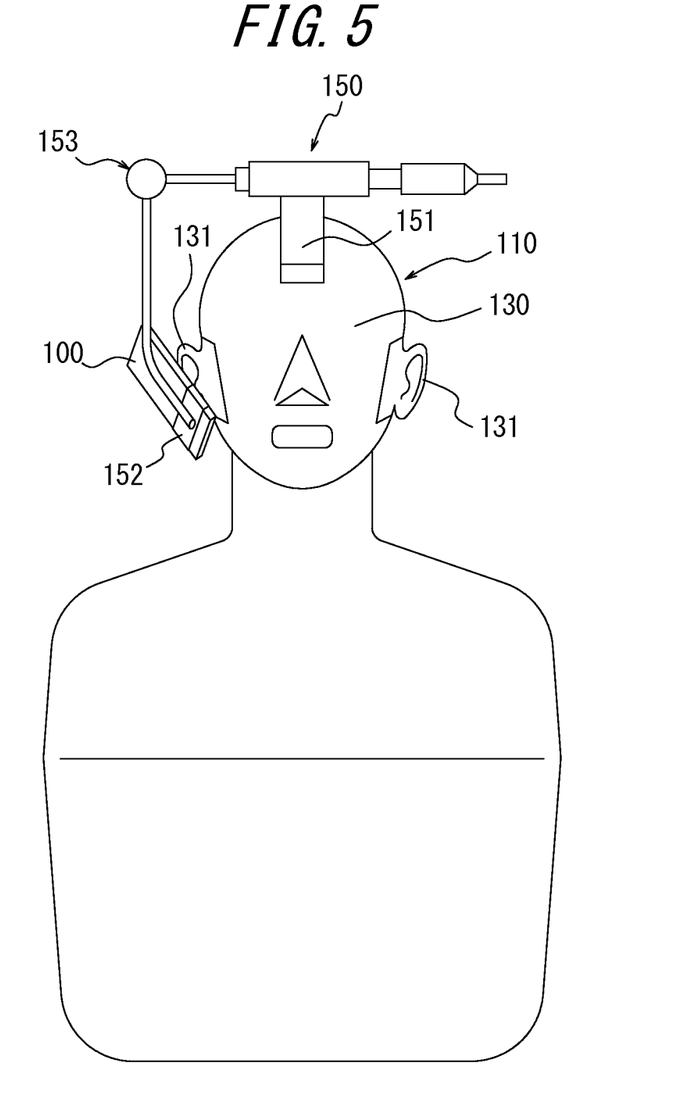
FIG. 5 is a diagram illustrating a schematic configuration of a measuring apparatus according to a second embodiment of the present invention.

FIG. 5 is a diagram illustrating a schematic configuration of a measuring apparatus according to a second embodiment of the present invention. A measuring apparatus 110 according to the present embodiment includes a human head model 130 and a holder 150 for holding the electronic device 100 to be measured. The human head model 130 may be, for example, HATS or KEMAR. An artificial ear 131 of the human head model 130 is removable from the human head model 130.

Figure 6A:
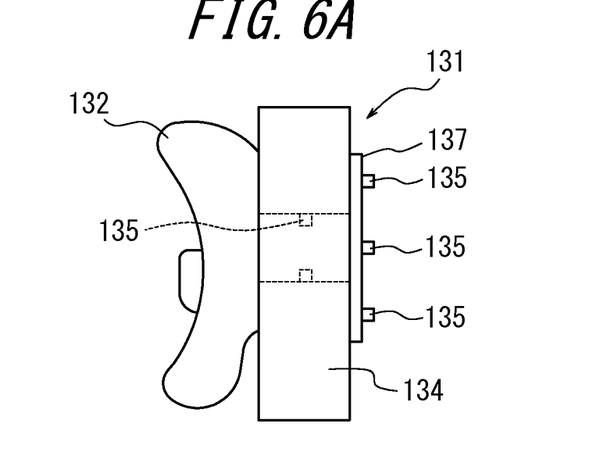
FIGS. 6A and 6B are detailed diagrams of portions of the measuring apparatus in FIG. 5.
Figure 6B:
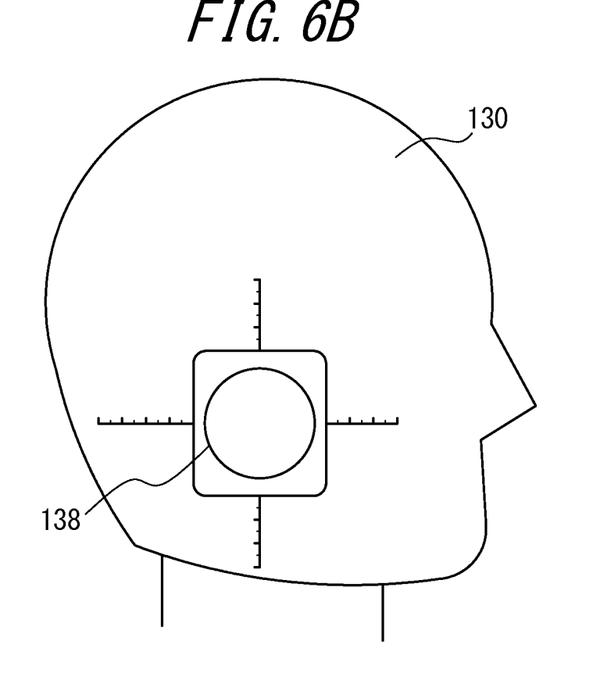

The artificial ear 131, as illustrated in a side view thereof removed from the human head model 130 in FIG. 6A, includes an ear model 132 similar to the ear simulator 50 of the first embodiment, an artificial ear canal unit 134 connected to the ear model 132 and having an artificial ear canal 133, and an artificial eardrum 137 in the form of a film disposed at an end of the artificial ear canal unit 134. At a periphery of an opening of the artificial ear canal 133 of the artificial ear canal unit 134, as with the ear simulator 50 of the first embodiment, vibration detectors 135 having the vibration detection elements are disposed. The artificial ear 131, as illustrated in a side view of the human head model 130 from which the artificial ear 131 is removed, is removably mounted on a mounting portion 138 formed on a side face of the human head model 130.

The holder 150 is removably attached to the human head model 130 and includes a head attachment unit 151 for fixing the holder 150 to the human head model 130, a supporter 152 for supporting the electronic device 100 to be measured, and an articulated arm 153 for connecting the head attachment unit 151 and the supporter 152. The holder 150 may adjust, via the articulated arm 153, the pressure on the artificial ear 131 applied by the electronic device 100 supported by the supporter 152 and the contact position of the electronic device 100, in a manner similar to the holder 70 of the first embodiment.

According to the measuring apparatus 110 of the present embodiment, an effect similar to that of the measuring apparatus 10 of the first embodiment may be obtained. According to the present embodiment, especially, since the artificial ear 131 for detecting the vibration is removably mounted on the human head model 130 for the evaluation of the electronic device 100, an evaluation further meeting an actual using manner considering an effect of the head portion may be achieved.

Note that the present invention is not limited to the above embodiments but may be varied or modified in a variety of manners. For example, although the above embodiments assume that the electronic device 100 to be measured is the mobile phone such as the smart phone having the panel 102 functioning as the vibrator, an electronic device such as a folding mobile phone having a panel which contacts the human ear when being used for calling or the like may also be evaluated. Further, not only the mobile phone but also other piezoelectric receivers may be evaluated as well.

Third Embodiment

Next, an example of the measuring method using the measuring apparatus according to the present invention will be described.

For example, the following measuring steps allows for various determinations. (1) An electronic device that generates vibration is mounted on the measuring apparatus in a predetermined position applying a predetermined pressure (approximately between 0 N and 10 N). (2) The electronic device is driven by a predetermined power. (3) The measuring apparatus obtains a result of detection by the vibration detector.

Although the above steps are basically good enough, a comparison to a result of measurement of an air conduction pressure obtained in the following manner is also effective. That is, either previously or after the fact, (1) an electronic device that generates vibration is mounted on the measuring apparatus in a predetermined position. At this time, a pressure of the electronic device 100 on the measuring apparatus may be 0 (zero) N, for a measurement of the air conduction volume. (2) The electronic device is driven by a predetermined power. (3) A normal air conduction volume is measured by a measuring apparatus having a microphone attached in a hollow manner inside the ear canal of the ear model of a conventionally known human body model such as HATS and KEMAR having no eardrum. (4) Then, a result of measurement of the vibration amount of the artificial eardrum obtained by the measuring apparatus of the present invention is linked to the result of measurement of the air conduction volume. Thereby, what is called a correlation, i.e., a transfer function between the air conduction volume and the artificial eardrum may be easily obtained. In this case, when the same electronic device is used, it means that each of the air conduction volume and the vibration amount in association with the same applied power is measured. That is, each correlation of the same electronic device is obtained.

On the other hand, a measurement as follows using another electronic device is also effective. That is, by using a speaker outputting the air conduction volume of 150 dB, the vibration amount when the electronic device is driven by application of the same power is detected by the measuring apparatus of the present invention. This means a measurement of the vibration amount of the artificial eardrum for a sound of 150 dB.

Next, by using an electronic device for transmitting a sound by a vibration sound alone, or by the vibration sound together with the air conduction sound, a vibration amount corresponding to the air conduction volume of 150 dB described above is detected. Thereby, a vibration amount corresponding to the air conduction volume of a common speaker may be measured. Note that, in using the electronic device that may output the sound through the vibration transmission and the air conduction sound together, a combination of the sound through the vibration transmission and the air conduction sound is measured as the vibration amount corresponding to approximately 150 dB. In using the electronic device that performs the vibration transmission alone, the detection of the vibration amount corresponds to a measurement of the vibration amount of the air conduction volume of approximately 150 dB.

The measuring method used for a comparison as described above may specify, to a certain level, the vibration amount of the artificial eardrum corresponding to a high volume which is considered to impose a risk of breaking the human eardrum due to the air conduction volume. Accordingly, the measuring method may contribute to production of safety-conscious electronic devices such as by limiting a maximum vibration amount based on thus obtained knowledge. Also, since the correlation between the air conduction volume and the vibration amount of the artificial eardrum may be obtained, designing and the like of mobile electronic devices for hearing-impaired people, for example, is facilitated. That is, it is facilitated to set a minimum or a maximum vibration amount by using data on hearing abilities of the hearing-impaired people on a basis of the air conduction sound preliminarily obtained in a hospital and the like.

REFERENCE SIGNS LIST 10 measuring apparatus
30 base
50 ear simulator
51 ear model
52 artificial ear canal unit
53 artificial ear canal
54 support member
55 vibration detector
56 vibration detection element
57 artificial eardrum
70 holder
71 supporter
72 arm
73 movement adjuster
75 signal processor
76 output device
100 electronic device
101 housing
102 panel (vibrator)
110 measuring apparatus
130 head model
131 artificial ear
132 ear model
133 artificial ear canal
134 artificial ear canal unit
135 vibration detector
137 artificial eardrum
138 mounting portion
150 holder
151 head attachment unit
152 supporter
153 articulated arm

The invention claimed is:

1. A measuring apparatus comprising:
an ear simulator for simulating the human ear, and
a vibration detector disposed on an artificial eardrum formed in the ear simulator, wherein
an electronic device delivers a sound through vibration transmission from a vibrator retained in a housing held against an external surface of an ear model, wherein
the ear simulator includes the ear model, an artificial ear canal unit connected to the ear model, and the artificial eardrum connected to the artificial ear canal unit, and
the artificial eardrum is separated from the ear model by an entirety of the artificial ear canal unit.

2. The measuring apparatus according to claim 1, further comprising a human head model comprising the ear simulator, wherein the ear simulator comprises an artificial ear removably mounted on the head model.

3. The measuring apparatus according to claim 1, wherein an artificial ear canal is formed in the artificial ear canal unit.

4. The measuring apparatus according to claim 3, wherein the artificial ear canal has a length of 20 mm to 40 mm.

5. The measuring apparatus according to claim 1, wherein the artificial eardrum has a thickness of 0.1 mm to 2 mm.

6. The measuring apparatus according to claim 3, wherein the artificial eardrum has an area of 0.5 cm² to 2.5 cm² that is exposed to the artificial ear canal of the artificial ear canal unit.

7. The measuring apparatus according to claim 1, further comprising a holder for holding the electronic device.

8. The measuring apparatus according to claim 7, wherein the holder supports at least two positions of the electronic device in a manner by which a human holds the electronic device against the human's ear.

9. The measuring apparatus according to claim 7, wherein the holder is adjustable to move in a direction holding the electronic device against the ear simulator.

10. The measuring apparatus according to claim 7, wherein the holder is adjustable to rotate in the direction holding the electronic device against the ear simulator.

11. The measuring apparatus according to claim 9, wherein the holder may adjust a pressure of the vibrator on the ear simulator in a range of 0 N to 10 N.

12. The measuring apparatus according to claim 9, wherein the holder may adjust the pressure of the vibrator on the ear simulator in a range of 3 N to 8 N.

13. The measuring apparatus according to claim 7, wherein the holder may change a contact position of the electronic device to the ear simulator by adjusting the electronic device in a vertical direction thereof with respect to the ear simulator.

14. The measuring apparatus according to claim 13, wherein the contact position includes a position in which the electronic device contacts the ear simulator such that the vibrator covers the ear simulator.

15. The measuring apparatus according to claim 13, wherein the contact position includes a position in which the electronic device contacts the ear simulator such that the vibrator partially contacts the ear simulator.

16. The measuring apparatus according to claim 1, wherein the ear simulator includes a portion formed of a material in conformity with IEC 60318-7.

17. The measuring apparatus according to claim 1, wherein the vibration detector includes a plurality of vibration detection elements arranged on the artificial eardrum.

18. The measuring apparatus according to claim 1, wherein the vibration detector includes a vibration detection element arranged at a periphery of the artificial ear canal.

19. A measuring method for evaluating an electronic device, the measuring method comprising a step of:
holding the vibrator against an ear simulator for simulating the human ear and detecting, by a vibration detector, vibration of the vibrator transmitted to an artificial eardrum formed in the ear simulator, wherein
the electronic device delivers a sound through vibration of a vibrator retained in a housing held against an external surface of an ear model, wherein
the ear simulator includes the ear model, an artificial ear canal unit connected to the ear model, and the artificial eardrum connected to the artificial ear canal unit, and
the artificial eardrum is separated from the ear model by an entirety of the artificial ear canal unit.

20. An ear simulator for simulating the human ear comprising an artificial ear canal unit and an artificial eardrum, wherein
the ear simulator is configured so that an electronic device delivers a sound through vibration transmission from a vibrator retained in a housing held against an external surface of an ear model, wherein
the ear simulator includes the ear model, an artificial ear canal unit connected to the ear model, and the artificial eardrum connected to the artificial ear canal unit, and
the artificial eardrum is separated from the ear model by an entirety of the artificial ear canal unit.

21. The ear simulator according to claim 20, wherein the artificial ear canal unit and the artificial eardrum are integrally formed from the same material.

22. The ear simulator according to claim 20, wherein the artificial eardrum is bonded or welded to the artificial ear canal.

23. An ear simulator for detecting vibration comprising the ear simulator according to claim 20 and a vibration detector disposed on the artificial eardrum of the ear simulator.

24. The ear simulator for detecting vibration according to claim 23, wherein the vibration detector is embedded in, or fixed to, the ear simulator.

25. A head model comprising the ear simulator according to claim 20 and an artificial head unit.

26. A head model for detecting vibration comprising the ear simulator for detecting vibration according to claim 23 and an artificial head unit.

27. A measuring method for comprising a step of:
comparing a vibration amount of the electronic device measured at the artificial eardrum of the measuring apparatus according to claim 1 and an air conduction volume of the electronic device that generates an air conduction sound measured by a microphone provided inside an artificial ear canal of an ear model having no artificial eardrum, and
obtaining a correlation between the air conduction volume and the vibration amount.

28. The measuring method according to claim 27, wherein the measurement is taken place for each pressure by changing the pressure on the measuring apparatus applied by the electronic device.

* * * * *